United States Patent
Frohberg et al.

(10) Patent No.: US 9,920,138 B2
(45) Date of Patent: Mar. 20, 2018

(54) ALTERNAN DERIVATIVES

(75) Inventors: Claus Frohberg, Kleinmachnow (DE); Waltraud Vorwerg, Potsdam (DE); Sylvia Radosta, Nuthetal (DE)

(73) Assignee: Bayer Intellectual Property GMBH, Monheim Am Rhein (DE)

( * ) Notice: Subject to any disclaimer, the term of this patent is extended or adjusted under 35 U.S.C. 154(b) by 1394 days.

(21) Appl. No.: 13/124,649

(22) PCT Filed: Oct. 16, 2009

(86) PCT No.: PCT/EP2009/007579
§ 371 (c)(1),
(2), (4) Date: Apr. 15, 2011

(87) PCT Pub. No.: WO2010/043423
PCT Pub. Date: Apr. 22, 2010

(65) Prior Publication Data
US 2011/0200538 A1 Aug. 18, 2011

Related U.S. Application Data

(60) Provisional application No. 61/196,425, filed on Oct. 17, 2008.

(30) Foreign Application Priority Data

Oct. 17, 2008 (EP) ..................... 08166936

(51) Int. Cl.
| | |
|---|---|
| C08B 37/00 | (2006.01) |
| A61K 8/73 | (2006.01) |
| A61Q 19/00 | (2006.01) |
| A23L 29/10 | (2016.01) |
| A23L 29/269 | (2016.01) |

(52) U.S. Cl.
CPC .......... *C08B 37/0009* (2013.01); *A23L 29/10* (2016.08); *A23L 29/273* (2016.08); *A61K 8/73* (2013.01); *A61Q 19/00* (2013.01); *A61K 2800/48* (2013.01); *A61K 2800/85* (2013.01)

(58) Field of Classification Search
None
See application file for complete search history.

(56) References Cited

U.S. PATENT DOCUMENTS

| 2,461,139 A | 2/1949 | Caldwell et al. |
| 2,661,349 A | 12/1953 | Caldwell et al. |
| 2003/0229923 A1 | 12/2003 | Kossmann et al. |

FOREIGN PATENT DOCUMENTS

| GB | 0 517 398 A | 1/1940 |
| WO | WO 2000/0047727 | 8/2000 |
| WO | WO 2003/0010177 | 2/2003 |
| WO | WO 2006/088884 | 8/2006 |

OTHER PUBLICATIONS

Leathers, T., et al., "Characterization of a novel modified alternan," Carbohydrate Polymers 54: 107-113 (2003).*
Čížová, A., et al., "Octenylsuccinate Derivatives of Carboxymethyl Starch—Synthesis and Properties," Starch 59: 482-492 (published on-line Oct. 8, 2007).*
Robyt, J., "Structure, Biosynthesis, and Uses of Nonstarch Polysaccharides: Dextran, Alternan, Pullulan, and Algin," Dev. Carbodydrate Chem 1992: 261-292.*
Biely et al., European Journal of Biochemistry, vol. 226, pp. 633-639 (1994).
Cote and Robyt, Carbohydrate Research, vol. 101, pp. 57-74 (1982).
Cote et al., Chapter 8: "Chemistry of Novel Foods", Carol Steam, IL: Allured Publishing Corp., pp. 95-110, ISBN 093171057 (1997).
Cote, Carbohydrate Polymers, vol. 19, pp. 249-252 (1992).
Jeanes, Journal of the American Chemical Society, vol. 76, pp. 5041-5052 (1954).
Joucla et al, FEBS Letters, vol. 580, pp. 763-768 (2006).
Kruger et al., Starch Chemistry and Technology, Chapter XV, pp. 369-401 (1967).
Misaki et al., Carbohydrate Research, vol. 84, pp. 273-285 (1980).
Raemaekers and Vandamme, Journal of Chemical Technology and Biotechnology, vol. 69, pp. 470-478 (1997).
Roberts, "Starch Chemistry and Technology" Ed.: Whistler and Paschall, Academic Press, vol. II, Roberts, Chapter XIII, pp. 293-350 (1967).
Roberts, Starch Chemistry and Technology, Ed.: Whistler and Paschall, Academic Press, vol. I, Roberts, Chapter XIX, pp. 439-493 (1965).
Seymour et al., Carbohydrate Research, vol. 74, pp. 41-62 (1979).
International Search Report for International Application No. PCT/EP2009/007579, dated Feb. 25, 2010.
Written Opinion for International Application No. PCT/EP2009/007579, dated Feb. 25, 2010.
International Preliminary Report Patentability for International Application No. PCT/EP2009/007579, dated Apr. 19, 2011.
Leathers et al., Journal of Industrial Microbiology & Biotechnology, vol. 18, pp. 278-283 (1997).

* cited by examiner

Primary Examiner — David J Blanchard
Assistant Examiner — Daniel F Coughlin
(74) Attorney, Agent, or Firm — Arent Fox LLP (57) ABSTRACT

The present invention relates to alternan-carboxylic acid esters, to processes for the preparation of alternan-carboxylic acid esters, and to compositions comprising alternan-carboxylic acid esters and to the use of alternan-carboxylic acid esters. The invention relates to alternan-carboxylic acid esters which are emulsifiers.

40 Claims, 4 Drawing Sheets

ALTERNAN DERIVATIVES

CROSS-REFERENCE TO RELATED APPLICATIONS

This application is the national phase application of PCT/EP2009/007579, filed Oct. 16, 2009, which claims the benefit of EP 08166936.8, filed Oct. 17, 2008, and U.S. Provisional Patent Application 61/196,425, filed Oct. 17, 2008, the contents of each are hereby incorporated by reference in their entirety.

FIELD OF THE INVENTION

The present invention relates to alternan-carboxylic acid esters, to processes for the preparation of alternan-carboxylic acid esters and to compositions comprising alternan-carboxylic acid esters and to the use of alternan-carboxylic acid esters.

BACKGROUND OF THE INVENTION

Alternan (CAS registration No.: 136510-13-9) was described as early as 1954 by Jeanes (J. Am. Soc. 76, 5041-5052) as fraction S glucan produced extracellularly from *Leuconostoc mesenteroides* NRRL B-1335. Alternan is a polysaccharide composed of glucose units. The glucose units are linked with one another via alpha-1,6- and alpha-1,3 glycosidic bonds, with these two types of bond occurring predominantly alternating (Miasaki et al., 1980, Carbohydr. Res. 84, 273-285). In addition, alternan may comprise up to ca. 10% branchings (Seymour et al., 1979, Carbohydrate Research 74, 41-62). Since alternan has the alpha-1,3 glycosidic bonds occurring alternately with the alpha-1,6 in the main chain of the polymer and successive alpha-1,6 glycosidic bonds, occurring very rarely, if at all, it is differentiated from dextran, a glucose polymer consisting in the main chain of predominantly alpha-1,6 glycosidic bonds (CAS registration No.: 9004-54-0). Cote and Robyt (1982, Carbohydr. Res. 101, 57-74) therefore introduced the name alternan, which is generally valid today, for the specified fraction S glucan from *Leuconostoc mesenteroides* NRRL B-1335.

Native alternan has a mean molecular weight ($M_w$) of $10^6$-$10^7$, is relatively readily water-soluble and confers a low viscosity on aqueous solutions (WO 03 010177).

Derivatives of alternan known hitherto are limited in that the molecular weight of native alternan has been reduced by means of physical and/or biological (enzymatic) processes.

Through the degradation of native alternan with the enzyme isomaltodextranase, a so-called limit alternan (known analogously to limit dextrins, which are obtained upon the degradation of starch by means of isoamylase) has been prepared, which has a mean molecular weight of 3500. The rheological properties (viscosity in aqueous solution) of the limit alternan correspond approximately to those of maltodextrin, i.e. limit alternan confers a low viscosity and is water-soluble in high concentrations (>80% w/v) (Cote et al., 1997, Chapter 8 In: Spanier et al. (ed), "Chemistry of novel foods", Carol Steam, Ill.: Allured Publishing Corp., 95-110, ISBN 093171057X).

Upon incubating native alternan in the presence of fungi of the genus *Penicillium*, the molecular weight of the native alternan is likewise reduced (WO 03 010177). Depending on the incubation time, alternan with a molecular weight of $5$-$10 \times 10^5$ (4 days incubation time) or $1$-$5 \times 10^4$ (7 days incubation time) was obtained. Alternan-degrading enzymes could not be detected in the fungi used for this purpose, meaning that the mechanism for reducing the molecular weight of native alternan through fungi of the genus *Penicillium* is hitherto unexplained.

Furthermore, the average molecular weight has been reduced to less than $10^6$ through treatment with ultrasound (Cote, 1992, Carbohydr. Polymers 19, 249-252).

Alternan with a reduced molecular weight which has been obtained following incubation with fungi or which has been obtained through treatment with ultrasound has similarities with gum arabic as regards its rheological behavior. In contrast to the solubility in water of native alternan (12%-15% w/v), it is readily water-soluble (up to 50% w/v) and confers a low viscosity on the solution. With regard to shear thinning, solutions of alternan with a reduced molecular weight exhibit a low pseudoelasticity and are approximately Newtonian liquids. In contrast to gum arabic, neither native alternan, nor alternan with a reduced molecular weight has emulsifying properties. On account of the specified rheological properties, both derivatives of alternan are proposed for the use as bulking agent, in particular in carbohydrate-containing foods (WO 03 010177).

Furthermore, alternan is a polymer which is degraded only by specific glucanases, Biley et al., 1994, Eur. J. Biochem. 226, 633-639. Such alternan-degrading glucanases are known from a few microorganisms. Consequently, alternan and alternan with a reduced molecular weight have been proposed as a low-calorie bulking agent for food products (Cote et al., 1997, Chapter 8 In: Spanier et al. (ed), "Chemistry of novel foods", Carol Steam, Ill.: Allured Publishing Corp., 95-110, ISBN 093171057X).

SUMMARY OF THE INVENTION

The object of the present invention is to provide alternan derivatives. Compared to native alternan, alternan derivatives have properties which make them suitable for certain applications. These alternan derivatives are particularly suitable for use in foods, pharmaceutical products or cosmetic products.

This object is achieved by the embodiments referred to in the claims.

DETAILED DESCRIPTION OF PREFERRED EMBODIMENTS

The present invention thus relates to alternan-carboxylic acid esters.

Surprisingly, it has been found that various alternan-carboxylic acid esters confer significantly higher viscosities on aqueous solutions than does native alternan, which only confers a low viscosity. Furthermore, in aqueous solutions of various alternan-carboxylic acid esters, there is a dependency of the viscosity conferred by them and the shear force acting on the solution. Solutions of various alternan-carboxylic acid esters, such as, for example, alternan-succinic acid esters, are therefore not Newtonian liquids. Native alternan has a solution character typical of Newtonian solutions with low interactions of the polymers, whereas alternan-succinic acid esters at identical concentration are gel-like, thus clearly recognizable interactions between the polymers arise. Consequently, various alternan-carboxylic acid esters are suitable particularly as structure-conferring additives in foods, pharmaceutical products or cosmetic products.

In connection with the present invention, the term "alternan" or "native alternan" is to be understood as meaning a polymer consisting of glucose units, where the glucose units of the main chain are linked almost exclusively in an alternating manner by means of alpha-1,6 and alpha-1,3 bonds. Alternan can have ca. 10% side chains which are formed by branchings of the main chains.

In connection with the present invention, the term "alternan-carboxylic acid ester" is to be understood as meaning alternan which comprises glucose molecules which have carboxylic acid ester bonds. Glucose molecules of alternan can have carboxylic acid ester bonds on the free OH groups in the C-2, C-3, C-4 and/or C-6 position of the carbon atoms. As a result of the alternating binding type of alternan, in each case all OH groups of the C-2 and C-4 positions of the glucose molecules and in each case ca. 50% of the OH groups of the C-3 and C-6 positions of the glucose molecules are available for the formation of an ester bond. Alternan-carboxylic acid esters according to the invention therefore comprise predominantly ester bonds at the C-2, C-3, C-4 and/or the C-6 positions of the glucose molecules of the polymer. Alternan-carboxylic acid esters can be depicted by the following formula (formula 1):

where R=
H,
a straight-chain or branched alkyl residue having 1 to 30 carbon atoms, preferably having 1 to 11 carbon atoms, which can carry one or more oxo, hydroxy, carboxy residues and/or which may be substituted by amino and/or halogen groups,
a straight-chain or branched alkenyl residue having 1 to 30 carbon atoms, preferably having 1 to 11 carbon atoms, which can carry one or more oxo, hydroxy, carboxy residues and/or which may be substituted by amino and/or halogen groups,
a straight-chain or branched alkadienyl residue having 1 to 30 carbon atoms, preferably having 1 to 11 carbon atoms, which can carry one or more oxo, hydroxy, carboxy residues and/or which may be substituted by amino, sulfur and/or halogen groups,
a straight-chain or branched alkatrienyl residue having 1 to 30 carbon atoms, preferably having 1 to 11 carbon atoms, which can carry one or more oxo, hydroxy, carboxy residues and/or which may be substituted by amino, sulfur and/or halogen groups,
a straight-chain or branched alkatetraenyl residue having 1 to 30 carbon atoms, preferably having 1 to 11 carbon atoms, which can carry one or more oxo, hydroxy, carboxy residues and/or which may be substituted by amino, sulfur and/or halogen groups,
a straight-chain or branched alkynyl residue having 1 to 30 carbon atoms, preferably having 1 to 11 carbon atoms, which can carry one or more oxo, hydroxy, carboxy residues and/or which may be substituted by amino, sulfur and/or halogen groups, and/or
an aryl residue which can carry one or more oxo, hydroxy, carboxy radicals and/or which may be substituted by amino, sulfur and/or halogen groups.

The alternan-carboxylic acid esters according to the invention may also be esters with saturated or mono- or polyunsaturated fatty acids.

In one preferred embodiment, the alternan-carboxylic acid esters according to the invention are carboxylic acid esters with the carboxylic acids listed in list 1 below, which may be named generically as alternan "trivial name" esters or alternan "chemical name" esters, where the terms "trivial name" or "chemical name" are replaced by one of the names listed under these terms in list 1 (e.g. alternan formic acid ester or alternan methanoic acid ester).

| List 1 | |
|---|---|
| Trivial name | Chemical name |
| Formic acid | (Methanoic acid) |
| Acetic acid | (Ethanoic acid) |
| Glyoxalic acid | (Oxoacetic acid) |
| Propionic acid | (Propanoic acid) |
| Lactic acid | (2-Hydroxypropanoic acid) |
| Pyruvic acid | (Oxopropanoic acid) |
| Pivalic acid | (2,2-Dimethylpropanoic acid) |
| Acrylic acid | (2-Propenoic acid) |
| Cinnamic acid | (3-Phenylpropenoic acid) |
| Benzoic acid | (Monophenylmethanoic acid) |
| Salicylic acid | (2-Hydroxybenzenecarboxylic acid) |
| Malonic acid | (1,3-Propanedioic acid) |
| Tartaric acid | (2,3-Dihydroxybutanedioic acid) |
| Succinic acid | (Butanedioic acid, succinyl acid) |
| Octenylsuccinic acid | (2-Octen-1-ylsuccinic acid) |
| Dodecenylsuccinic acid | (2-Dodecen-1-ylsuccinic acid) |
| Malic acid | (2-Hydroxybutanedioic acid) |
| Aspartic acid | (2-Aminobutanedioic acid) |
| Maleic acid | (cis-Butenedioic acid) |
| Fumaric acid | (trans-Butenedioic acid) |
| Itaconic acid | (cis-Methylenebutenedioic acid) |
| Glutaric acid | (Pentanedioic acid) |
| Adipic acid | (1,6-Hexanedioic acid) |
| Pimelic acid | (Heptanedioic acid) |
| o-Phthalic acid | (1,2-Benzenedicarboxylic acid) |
| m-Phthalic acid | (1,3-Benzenedicarboxylic acid) |
| p-Phthalic acid | (1,4-Benzenedicarboxylic acid) |
| Citric acid | (2-Hydroxypropane-1,2,3-tricarboxylic acid) |
| Butyric acid | (Butanoic acid) |
| Valeric acid | (Pentanoic acid) |
| Caproic acid | (Hexanoic acid) |
| Caprylic acid | (Octanoic acid) |
| Palmitic acid | (Hexadecanoic acid) |
| Stearic acid | (Octadecanoic acid) |
| Cerotic acid | (Hexacosanoic acid) |
| Palmitoleic acid | ((9z)-Hexadeca-9-enoic acid) |
| Oleic acid | ((9z)-Octadeca-9-enoic acid) |
| Erucic acid | ((13z)-Docosa-13-enoic acid) |
| Linoleic acid | ((9z,12z)-Octadeca-9,12-dienoic acid) |
| alpha-Linolenic acid | ((9z,12z,15z)-Octadeca-9,12,15-trienoic acid) |
| gamma-Linolenic acid | (6z,9z,12z)-Octadeca-6,9,12-trienoic acid |
| gamma-Arachidonic acid | (5z,8z,11z,14z)-Eicosa-5,8,11,14-tetraenoic acid |

The alternan-carboxylic acid esters according to the invention are particularly preferably carboxylic acid esters with dicarboxylic acids, such as, for example, alternan-fumaric acid ester (alternan-trans-butenedioic acid ester), alternan-itaconic acid ester (alternan-cis-methylenebutenedioic acid ester), alternan-glutaric acid ester (alternan-pentanedioic acid ester) or alternan-phthalic acid ester (alternan-benzenedicarboxylic acid ester). It is obvious to the person skilled in the art that particularly alternan-carboxylic acid esters with di- or tricarboxylic acids may, depending on the composition of the solution in which they are present, also be present as salts. Consequently, salts of alternan-carboxylic acid esters according to the invention are also provided by the present invention.

The alternan-carboxylic acid esters according to the invention are particularly preferably alternan-acetic acid ester (alternan-ethanoic acid ester), alternan-succinic acid ester (alternan-butanedioic acid ester, alternan-succinyl acid ester) or alternan-octenylsuccinic acid ester (alternan-2-octen-1-ylsuccinic acid ester, alternan-octenyl succinate ester).

Alternan-carboxylic acid esters according to the invention can have a degree of substitution (DS) of from 0.005 to 3. In one preferred embodiment, alternan-carboxylic acid esters according to the invention have a degree of substitution of from 0.005 to 2.0, preferably from 0.008 to 1.0, particularly preferably from 0.01 to 1.0, particularly preferably from 0.01 to 0.5 and especially preferably from 0.01 to 0.04.

In connection with the present invention, the term "degree of substitution (DS)" is to be understood as meaning the molar degree of substitution which indicates how many moles of substituent are present in bonded form per mole of glucose. Since all C-2 and C-4 positions and in each case ca. 50% of the C-3 and C-6 positions of the glucose molecules of alternan can be substituted, the maximum degree of substitution is 3.

Alternan-carboxylic acid esters according to the invention preferably have a weight-average molecular weight ($M_w$) of from $10^5$ to $10^8$, preferably from $10^6$ to $10^8$, particularly preferably $5 \times 10^6$ to $10^8$ and especially preferably from $5 \times 10^6$ to $5 \times 10^7$. Methods for determining the weight-average molecular weight ($M_w$) are known to the person skilled in the art and include, for example, determination methods by means of GPC (Gel Permeation Chromatography) coupled with corresponding detection methods such as, for example, MALLS (Multi Angle Laser Light Scattering). One method of determining the weight-average molecular weight ($M_w$) preferred in connection with the present invention is described under General Methods, point 3. Alternan-carboxylic acid esters can be prepared using methods known to the person skilled in the art analogously to the derivatization of other carbohydrate polymers such as e.g. starch or cellulose. Methods for the esterification of starches are known to the person skilled in the art and described, inter alia, in U.S. Pat. No. 2,461,139, U.S. Pat. No. 2,661,349, in "Starch Chemistry and Technology" Ed.: Whistler and Paschall, Academic Press, 1965, Volume I, Roberts, Chapter XIX, 439-493, in "Starch Chemistry and Technology" Ed.: Whistler and Paschall, Academic Press, 1967, Volume II, Roberts, Chapter XIII, 293-350 and Kruger and Rutenberg, Chapter XV, 369-401. Native starch and cellulose are water-insoluble substances which are derivatized either in native form or in dissolved form. For this, either suitable solvents are used or, in the case of starch, this is firstly, through elevated temperatures, gelatinized in aqueous solutions or dissolved in suitable solvents (e.g. formamide). Since alternan is a relatively readily water-soluble polymer, it is possible to prepare alternan-carboxylic acid esters in aqueous solutions, although it is also possible to use other customary (organic) solvents, such as, for example, formamide. Consequently, compared with the esterification of e.g. starch or cellulose, the preparation of alternan-carboxylic acid esters offers the advantage that no particular process steps are required for the dissolving or suspending before an esterification can be carried out.

On account of their insolubility in water, native starch and cellulose are often esterified in aqueous particulate suspensions. This leads, inter alia, to the fact that the degree of esterification within a particle varies from the outside inwards, i.e. the degree of ester bonds decreases from the surface to the inside of the particles. By contrast, alternan is relatively readily soluble in water, meaning that it has the advantage that, when carrying out the reaction in aqueous solutions, a uniform distribution of the ester bonds over the dissolved molecules can be achieved. Carrying out the esterification reaction in aqueous solution additionally offers the advantage that no organic solvents are produced which have to be separately separated off and/or disposed of.

The esterification of polymers consisting of glucose units, such as, for example, starch, can be carried out by various processes, e.g. by direct esterification by means of carboxylic acids or by esterification by means of carboxylic anhydrides, carboxylic acid halides or vinyl esters.

For the esterification by means of various specified processes, alternan may be in the form of a saturated solution. Preference is given to using an amount of alternan of from 1% to 18%, preferably 3% to 15%.

The alternan used in the esterification reaction can have various molecular weights. It may be native alternan, or alternan with a reduced molecular weight, which has been reduced in its molecular weight enzymatically, through the effect of ultrasound or through incubation with fungi.

During the direct esterification with carboxylic anhydrides, the reaction takes place in aqueous solutions of carboxylic acids. Preferably, for this, a strong carboxylic acid (e.g. formic acid) is used, particularly if high degrees of substitution are to be achieved. To increase the reactivity it is also possible to add catalysts, such as, for example, sulfuric acid or halides.

The reaction of alternan with carboxylic acid anhydrides or carboxylic acid halides can be carried out either in alkaline, aqueous solutions, or it is carried out in solutions to which a catalyst, such as, for example, pyridine, has been added. Pyridine-catalyzed reactions are preferably carried out in organic solvents (e.g. formamide). By adding pyridine to the solution, it is possible to establish an alkaline pH. Furthermore, pyridine serves here as catalyst of the reaction.

Compared to other polymers consisting of glucose units, such as, for example, starch, alternan offers the advantage that it has good stability in solutions over a broad pH range. By contrast, other polymers consisting of glucose units, in particular starches, have a considerably lower stability, which leads to the significant reduction in the molecular weight of these substances during the esterification reaction. This often leads to these substances having too low a molecular weight following esterification to exhibit the properties which are supposed to be achieved by the esterification reaction. The considerably higher stability of alternan compared to other polymers consisting of glucose units, such as e.g. starch, over a broad range of the pH scale permits, for example, a direct esterification of alternan by means of carboxylic acids without considerably reducing the molecular weight of the alternan. Since said processes for the esterification of polymers consisting of glucose units are carried out in an acidic or a basic medium and alternan is stable in solutions over a broad pH range, all processes known to the person skilled in the art for the esterification of polymers consisting of glucose units, such as e.g. starch, can be used in principle to prepare alternan-carboxylic acid esters.

The present invention also encompasses a process for the preparation of alternan-carboxylic acid esters, in which alternan is reacted with an esterifying agent. The esterifying agent is preferably a carboxylic acid, a carboxylic acid anhydride, carboxylic acid halide or a vinyl ester.

As regards the present invention, alternan-carboxylic acid esters are preferably prepared by firstly dissolving alternan in water and adjusting the pH of this solution to a basic value for activating the reactivity of the alternan (aqueous, alkaline process). An esterifying agent is then added to this solution. In order to stop the esterification reaction, the pH of the reaction mixture can be reduced to a neutral or slightly acidic level (e.g. pH 6.0 to 6.5). Resulting water-soluble alternan-carboxylic acid esters can then be isolated using methods known to the person skilled in the art. A simple isolation is e.g. the precipitation of the alternan-carboxylic acid esters with the help of suitable precipitating agents (e.g. ethanol). To further improve the purity of the alternan-carboxylic acid esters, these can be washed one or more times, after the precipitation, using suitable (e.g. ethanol-containing) solutions. If required, a drying of the alternan-carboxylic acid esters (e.g. under reduced pressure, freeze-drying, spray-drying) can take place.

Suitable esterifying agents for the aqueous, alkaline process are, besides carboxylic acid halides, in particular carboxylic acid anhydrides or vinyl esters.

In the case of the aqueous, alkaline process, the pH of the solution should be more than 7. The solution is preferably adjusted to a pH between 7 and 12, preferably from 7.5 to 10, particularly preferably from 8 to 10 and especially preferably from 8.0 to 9.0.

To activate the alternan and to adjust the pH to the preferred value, any desired alkaline agent may be used. Suitable alkaline agents are, for example, hydroxides of alkali metals or alkaline earth metals or hydroxides, oxides or carbonates of main groups I and II of the Periodic Table of the Elements. The alkaline agents are preferably sodium hydroxide, potassium hydroxide, calcium hydroxide, ammonium hydroxide, magnesium hydroxide, sodium carbonate or trisodium phosphate. Particular preference is given to using sodium hydroxide.

Since, as a result of the esterification reaction and the participation of alkaline agents, the pH of the reaction mixture drops, it should be controlled through the further addition of an alkaline agent, particularly if high degrees of substitution of the alternan are desired. The addition can take place either sequentially, e.g. if a certain pH of the reaction mixture falls below a the desired value, or continuously. Alternatively, the pH of the reaction mixture can also be controlled through the continuous or sequential addition of a mixture of esterifying agent and/or alkaline agent.

The esterification reaction can be carried out at room temperature or else at elevated temperatures depending on the esterifying agent used. Preference is given to carrying out the reaction between 20° C. and 95° C., particularly preferably between 20° C. and 80° C., especially preferably at 20° C. to 60° C. and specifically preferably at 20° C. to 40° C.

The esterifying agents used in the aqueous, alkaline process are preferably carboxylic acid anhydrides or vinyl esters. In the processes according to the invention, preference is given to using anhydrides of the carboxylic acids specified in list 1 or anhydrides of fatty acids.

In an alternative possible process, alternan-carboxylic acid esters are prepared by adding pyridine to the reaction solution as catalyst. To increase the degree of substitution, pyridine can be added in excess. Suitable esterifying agents (acylating agents) in this process are the carboxylic acid anhydrides already specified. Esterifying agents which may be used in this process are, especially in relation to relatively long-chain fatty acids, also carboxylic acid halides, preferably carbonyl chlorides. The carboxylic acid halides are preferably halides of the carboxylic acids specified in list 1 or halides of fatty acids.

To prepare alternan-carboxylic acid mixed esters it is possible either to use different, said esterifying agents at the same time in a reaction, or it is possible to carry out different, said esterifying agents in successive reactions.

The present invention therefore also relates to alternan-carboxylic acid mixed esters. The alternan-carboxylic acid mixed esters are alternan molecules which have at least two different ester groups, the different ester groups being characterized in that their residue R stated in formula 1 is different. These are preferably alternan molecules which have been esterified with in each case at least two of the carboxylic acids specified in list 1 and/or with at least two fatty acids. Alternatively these are alternan molecules which have been esterified with at least one carboxylic acid specified in list 1 and at least one fatty acid.

As already described, solutions comprising alternan-carboxylic acid esters or alternan-carboxylic acid mixed esters can have a considerably higher viscosity compared to solutions comprising alternan. Solutions of alternan-carboxylic acid esters, in particular alternan-succinic acid esters or alternan-carboxylic acid mixed esters, can form gels above a concentration (about 5% in the case of alternan-succinic acid esters). Alternan-carboxylic acid esters or alternan-carboxylic acid mixed esters can additionally have the property that the resulting solutions have little turbidity. Alternan-carboxylic acid esters or alternan-carboxylic acid mixed esters can also serve for the stabilization of emulsions (e.g. alternan-succinic acid esters) or they can be used as emulsifier (e.g. alternan-octenylsuccinic acid ester).

The invention further provides an emulsifier which is an alternan-carboxylic acid ester according to the invention. The emulsifier is preferably an alternan-carboxylic acid ester with dicarboxylic acids, particularly preferably an alternan-carboxylic acid ester with dicarboxylic acids having 8 to 14 carbon atoms, preferably having 10 to 14 carbon atoms; it is particularly preferably alternan-octenylsuccinic acid ester.

The emulsifier according to the invention preferably has a degree of substitution (DS) of from 0.001 to 0.05, preferably from 0.003 to 0.04, preferably from 0.008 to 0.03 and especially preferably from 0.01 to 0.03.

The invention further provides emulsions comprising alternan-carboxylic acid esters according to the invention or alternan-carboxylic acid mixed esters according to the invention as emulsifier. The emulsions according to the invention are preferably emulsions comprising alternan-carboxylic acid esters with dicarboxylic acids, particularly preferably emulsions comprising alternan-carboxylic acid esters with dicarboxylic acids having 8 to 14 carbon atoms, preferably having 10 to 14 carbon atoms; they are particularly preferably emulsions comprising alternan-octenylsuccinic acid esters.

In connection with the present invention, the term emulsion should be understood as meaning a finely divided mixture of two normally immiscible substances without visible separation. Preferred mixtures are dispersions.

Besides a hydrophilic (e.g. water) and a lipophilic substance (e.g. oil), emulsions according to the invention preferably comprise an alternan-carboxylic acid ester according to the invention. Here, said emulsions comprise the alternan-carboxylic acid esters according to the invention in a concentration of at least 0.1%, preferably of at least 0.3%, preferably of at least 0.5%, particularly preferably of at least 1.0% and especially preferably of at least 3.0%, measured in weight fractions of the emulsifier per volume of the emulsion.

These are preferably emulsions which comprise alternan-carboxylic acid esters according to the invention in a concentration range from 0.05% to 5%, preferably from 0.1% to 5.0%, particularly preferably from 0.5% to 5% and especially preferably from 1.0% to 3%, measured in weight fractions of the emulsifier per volume of the emulsion.

The amount of emulsifier according to the invention used here can be adjusted according to the fraction of lipophilic substances in the mixture.

A further subject matter relates to a process for the preparation of an emulsion in which alternan-carboxylic acid esters according to the invention and a mixture consisting of immiscible substances are mixed together.

It is unimportant whether the emulsifier according to the invention is mixed in processes according to the invention for the preparation of an emulsion with solid substances and/or liquids. What matters is merely that the emulsifying effect is brought to bear.

Preferably, in the process according to the invention for the preparation of an emulsion, the preferred emulsifiers according to the invention already specified above are used.

The use of alternan-carboxylic acid esters or alternan-carboxylic acid mixed esters according to the invention as emulsifier is likewise provided by the invention.

The present invention further provides the use of an emulsifier according to the invention or of an emulsion according to the invention or of an emulsion obtainable by a process according to the invention for the preparation of an emulsion for the preparation of food or feed additives, of foods or feeds, of cosmetic products or of pharmaceutical products.

The present invention further provides the use of an alternan-carboxylic acid ester according to the invention or of an emulsifier according to the invention or of an emulsion according to the invention as surfactant. Preferably, the use as surfactant is the use in cleaning compositions (such as e.g. washing, rinsing or cleaning compositions) or in body care substances (such as e.g. shampoo, shower gel, soaps, creams) or the use as foaming agents.

In connection with the present invention, the term "surfactant" should be understood as meaning a substance which reduces the surface tension of a liquid or the interfacial tension between two phases and permits or supports the formation of dispersions.

On account of the specified properties of alternan-carboxylic acid esters, these can therefore be used in a large number of different products.

Consequently, the present invention further provides compositions comprising alternan-carboxylic acid esters according to the invention and/or alternan-carboxylic acid mixed esters according to the invention and/or emulsifiers according to the invention and/or emulsions according to the invention.

The compositions according to the invention are preferably foods (foodstuffs and luxuries), food compositions, cosmetic compositions or pharmaceutical compositions.

The food compositions according to the invention are preferably compositions comprising alternan-carboxylic acid esters according to the invention and/or alternan-carboxylic acid mixed esters according to the invention and/or emulsifiers according to the invention and/or emulsions according to the invention and (at least) one substance which is consumed by people for the purposes of nutrition. Substances which are consumed by people for the purposes of nutrition include, inter alia, roughage, minerals, water, carbohydrates, proteins, fats, vitamins, secondary vegetable materials, trace elements, aroma substances, flavorings and/or food additives.

The cosmetic compositions according to the invention are preferably compositions comprising alternan-carboxylic acid esters according to the invention and/or alternan-carboxylic acid mixed esters according to the invention and/or emulsifiers according to the invention and/or emulsions according to the invention and one or more ingredients listed under the INCI nomenclature (INCI: International Nomenclature Cosmetic Ingredients). Ingredients covered by the INCI nomenclature are published, inter alia, in "International Cosmetic Ingredient Dictionary and Handbook", 11th Edition, January 2006, Publisher: CTFA, ISBN: 1882621360. The cosmetic compositions are particularly preferably creams.

The pharmaceutical compositions according to the invention are preferably compositions comprising alternan-carboxylic acid esters according to the invention and/or alternan-carboxylic acid mixed esters according to the invention and/or emulsifiers according to the invention and/or emulsions according to the invention and (at least) one pharmacologically active substance.

Various alternan-carboxylic acid esters (such as e.g. alternan-succinic acid ester) or alternan-carboxylic acid mixed esters may be suitable, as a result of conferring viscosity and the formation of gels at a relatively low concentration, in particular for use in foods/food compositions in which a certain thickening ability is of relevance. They can therefore be used as viscosity regulator or gelling agent during manufacture and preparation (e.g. in milk products, bakery goods, beverages, desserts, jams, sauces, puddings etc.). Since alternan-carboxylic acid ester or alternan-carboxylic acid mixed ester solutions (such as e.g. alternan-succinic acid ester) only have a slight turbidity, they are therefore particularly suitable for use in foods which should or must have a clear appearance. The stabilizing effect and/or the emulsifying activity which various alternan-carboxylic acid esters or alternan-carboxylic acid mixed esters have on emulsions makes them particularly suitable for use in foods which have both lipophilic constituents (e.g. fats), and also hydrophilic constituents.

As regards cosmetic or pharmaceutical compositions, the viscosity-conferring properties of alternan-carboxylic acid esters or alternan-carboxylic acid mixed esters, as well their emulsion-stabilizing and/or emulsifying properties, are likewise of particular importance. They can therefore be e.g. constituents of tinctures, creams, lotions, salves, sun protection compositions, make-up compositions, dental cleaning compositions, body care and hair care compositions etc. Since various alternan-carboxylic acid esters (such as e.g. alternan-succinic acid ester) or alternan-carboxylic acid mixed esters can form gels, they are also particularly suitable for the preparation of hydrogels. As regards pharmaceutical compositions, alternan-carboxylic acid esters (such as e.g. alternan-succinic acid ester) or alternan-carboxylic acid mixed esters can be used as disintegrants, e.g. in tablets.

The invention further provides a process for the preparation of a composition in which alternan-carboxylic acid esters according to the invention and/or alternan-carboxylic acid mixed esters according to the invention and/or emulsifiers according to the invention and/or emulsions according to the invention are mixed with other substances or are added to these.

Preferably, processes according to the invention for the preparation of a composition relate to processes for the preparation of foods (foodstuffs and luxury foodstuffs), food compositions, processes for the preparation of cosmetic compositions or processes for the preparation of pharmaceutical compositions.

As regards processes for the preparation of foods (foodstuffs and luxuries) or food compositions, alternan-carboxylic acid esters according to the invention and/or alternan-carboxylic acid mixed esters according to the invention and/or emulsifiers according to the invention and/or emulsions according to the invention and (at least) one substance which is consumed by people for the purposes of nutrition, are mixed, or alternan-carboxylic acid esters according to the invention and/or alternan-carboxylic acid mixed esters according to the invention and/or emulsifiers according to the invention and/or emulsions according to the invention are added to such substances or substance mixtures (such as e.g. milk). The substances which are mixed with alternan-carboxylic acid esters and/or alternan-carboxylic acid mixed esters according to the invention and/or emulsifiers according to the invention and/or emulsions according to the invention are roughage, minerals, water, carbohydrates, proteins, fats, vitamins, secondary plant metabilites, trace elements, aroma substances, flavorings and/or food additives.

With regard to processes for the preparation of pharmaceutical compositions, alternan-carboxylic acid esters according to the invention and/or alternan-carboxylic acid mixed esters according to the invention and/or emulsifiers according to the invention and/or emulsions according to the invention and (at least) one pharmacologically active substance are mixed, or alternan-carboxylic acid esters according to the invention and/or alternan-carboxylic acid mixed esters according to the invention and/or emulsifiers according to the invention and/or emulsions according to the invention are added to such substances or material mixtures comprising said substances.

With regard to processes for the preparation of cosmetic compositions, alternan-carboxylic acid esters according to the invention and/or alternan-carboxylic acid mixed esters according to the invention and/or emulsifiers according to the invention and/or emulsions according to the invention and one or more of the ingredients listed under the INCI nomenclature (INCI: International Nomenclature Cosmetic Ingredients) are mixed, or alternan-carboxylic acid esters according to the invention and/or alternan-carboxylic acid mixed esters according to the invention and/or emulsifiers according to the invention and/or emulsions according to the invention are added to such substances or material mixtures comprising said substances.

Preferably, processes according to the invention for the preparation of a composition relate to processes for the preparation of a composition according to the invention.

The use of alternan-carboxylic acid esters and/or alternan-carboxylic acid mixed esters and/or emulsifiers according to the invention and/or emulsions according to the invention for the preparation of a composition according to the invention is likewise provided by the present invention.

Furthermore, the present invention relates to the use of alternan-carboxylic acid esters according to the invention or alternan-carboxylic acid mixed esters according to the invention and/or emulsifiers according to the invention and/or emulsions according to the invention for the preparation of foods or for the preparation of pharmaceutical compositions or for the preparation of cosmetic compositions.

GENERAL METHODS

1. Preparation of Alternan

Alternan can be prepared with the help of the enzyme alternansucrase. The enzyme alternansucrase can be prepared in various ways by processes known to the person skilled in the art.

The preparation of alternansucrase and alternan with the help of bacterial strains of the species *Leuconostoc mesenteroides* are described inter alia in Reamakers et al (1997, J. Chem. Tech. Biotechnol. 69, 470-478) or in WO 2006 088884 (see in particular example 1).

However, processes which use *Leuconostoc mesenteroides* bacterial strains for the preparation of the enzyme alternansucrase have the disadvantage that these strains also produce other sucrases, in particular dextransucrases. These other sucrases have hitherto been unable to be completely separated from alternansucrase. It is therefore a mixture of different enzymes. Consequently, the alternan prepared using such an enzyme mixture has, besides alternan, also dextran, at least in small amounts. To prepare pure alternans, methods for the preparation of alternansucrase by means of recombinant organisms are therefore to be preferred.

Processes for the preparation of alternansucrase prepared by means of recombinant organisms and for the preparation of alternan by means of the enzyme prepared in this way are described, inter alia, in WO 2000 47727, US 2003 229923 (see in particular examples 2, 5 and 8) or Joucla et al (2006, FEBS Letters 580, 763-768).

2. Determination of the Degree of Esterification

The degree of esterification of the various alternan derivatives was ascertained by means of alkaline saponification and subsequent acid-base titration. The percentage fraction of the substitution (mass of the substituent in %, based on the dry substance of the alternan derivatives) was determined.

Using the resulting values, the degree of substitution (DS) was ascertained in accordance with the following formula:

$$DS_x = 162 \times \% \; X / (100 \times M_x - \Delta M \times \% \; X)$$

% X=Fraction (in %) of the mass of the analytically determined group (substituent) of the mass of the dry substance
Mx=Molar mass of the analytically determined group
ΔM=MS−ML
MS=Molar mass of the substituent
ML=Molar mass of the saponified group

3. Determination of the Molar Mass Distribution by Means of GPC-MALLS

To determine the molar mass distribution by means of gel permeation chromatography, the following instruments were used:
Instruments: Alliance 2695 separation module from Waters, DRI detector 2414 from Waters, MALLS detector Dawn-HELEOS from Wyatt Technology Inc., Santa Barbara, USA, wavelength λ=658 nm and a K5 flow cell
Columns: SUPREMA gel column set (PSS Mainz), exclusion limits S30000 with $10^8$-$10^6$, S1000 with $2 \cdot 10^6$-$5 \cdot 10^4$, S100 with $10^5$-$10^3$
Eluent: 0.5 m $NaNO_3$
Temperature: 30° C.
To evaluate the data obtained, Astra Software 5.3.0.18 was used.

4. Rheological Characterization by Means of Rheometer

To determine the rheological properties, the following instruments were used with the stated (adjustable) parameters:
Instrument: Rheometer CVO 120HR from Malvern (Bohlin)
Parameters
Torque: 0.0001-120 mNm (6 powers of ten)
Torque resolution: better than $10^{-9}$ Nm
Angle resolution: $5 \cdot 10^{-5}$ rad
Frequency range: $10^{-5}$-150 Hz
Speed range: <$10^{-5}$-3100 $min^{-1}$
With the help of the specified instrument, the storage modulus (G') and loss modulus (G") were determined as a function of the frequency at constant deformation/shear stress (frequency sweep) and as a function of the shear stress at constant frequency (stress sweep).

5. Viscosity Determination by Means of RVA

The material is dissolved in distilled $H_2O$ and homogenized using an Ultra-Turrax T 25 digital (IKA-Werke GMBH & CO. KG, D-79219 Staufen, Germany) for 1 minute at 9000 rpm. 27 ml of 10% strength solution are used in an RVA beaker in a Rapid Visco Analyzer (Newport Scientific Pty Ltd., Investment Support Group, Warriewod NSW 2102, Australia) to measure the viscosity. The instrument is operated in accordance with the manufacturer's instructions. Here, the viscosity values are stated in centipoise (1 cP=1 mPa×s) in accordance with the manufacturer's operating instructions. To determine the viscosity of the aqueous solution of the material, the suspension is firstly stirred at 25° C. for 10 seconds at 1200 rpm, then the temperature is kept constant at 25° C. and the mixture is stirred at a stirring speed of 1000 rpm for a further 2 minutes and 50 seconds. During the total time of 3 minutes, the viscosity is determined in centipoise (cP).

EXAMPLES

1. Alternan-Acetic Acid Ester (Alternan-Acetyl Ester)

a) Preparation

Firstly 80 ml of demineralized water were initially introduced in a 250 ml beaker and then 10 g of alternan were dissolved with constant stirring by means of a magnetic stirrer. After dissolving the alternan, a pH of 8.5 was established using 0.5M NaOH (Merck). In two separate mixtures, the reaction was started by adding in each case 1 ml (sample 1) or 2 ml (sample 2) of vinyl acetate (Merck). Throughout the entire reaction time, the pH was kept constant using a 0.5M NaOH solution (Merck) using an automatic titrater (pH-Stat, Metrohm 719 S Titrino). The reaction was carried out at 23° C.

The reaction was ended by neutralization (pH≈6.3) with the help of 0.5M HCl (Merck), and, to precipitate out the alternan, the reaction mixture was poured into a 500 ml beaker with twice the volume of ethanol (denatured, Monopoly Administration). After stirring for 5 min using a magnetic bar, the alternan derivative was separated off from the mixture with the help of a vacuum suction filter (φ 100 mm), then the filter cake was resuspended for washing in ca. 100 ml of ethanol/demineralized water (80:20; v:v). The washing procedure was repeated twice, and the filter cake was then granulated using a laboratory sieve (φ 200 mm, mesh width 3 mm) and then the granules were dried in the air for two days. Prior to characterizing the product, the agglomerates were comminuted using a laboratory mill (IKA model A 10).

b) Characterization

The turbidity measurement was carried out using a 0.5% strength solution of alternan or alternan derivatives. 49.75 g of demineralized water were weighed into a 150 ml beaker and 0.25 g of alternan/alternan derivatives were dissolved therein at room temperature and with constant stirring using a magnetic stirrer. The turbidity was measured after stirring for 1 hour with the help of a photometer (PM 200 from Rühle, Berlin) using a filter 525 nm and a cell of 1 cm in thickness.

The acetic acid fraction (acetyl content) of the alternan-carboxylic acid esters was determined in accordance with the method described above under General Methods under point 2.

TABLE 1

Turbidity measurement (column 4) and amount of acetyl content (column 5) of alternan-acetic acid esters which have been prepared using different amounts of vinyl acetate.

| Sample | Amount of vinyl acetate | Reaction time | Turbidity [absorbance 525 nm] | Acetyl content (DS value) |
|---|---|---|---|---|
| Reference | — | — | 0.30 | — |
| Sample 2 | 1 ml | 1 h | 0.24 | 0.062 |
| Sample 3 | 1 ml | 2 h | 0.23 | 0.053 |
| Sample 3 | 2 ml | 2 h | 0.23 | 0.048 |

The amount of vinyl acetate used in the esterification reaction and the duration of the reaction are shown in columns 2 and 3, respectively. The reference (column 1) referred to is native alternan which has been used as starting material in the reaction. Samples 1, 2 and 3 (column 1) refer to alternan-acetic acid esters which have been prepared by means of different reaction conditions.

2. Alternan-Succinic Acid Esters (Alternan-Succinate)

a) Preparation 50 g of alternan (dry weight) were initially introduced in a 1 liter jacketed reactor, dissolved in demineralized water and rendered alkaline using an automatic titrater. Succinic acid anhydride was slowly added. After the reaction had ended, the pH was adjusted to 6.5. The resulting alternan-succinic acid ester was precipitated out with ethanol, washed and dried in vacuo in a drying cabinet.

b) Degree of Substitution

The degree of substitution (DS value) of the resulting alternan-succinic acid esters was determined in accordance with the method described under General Methods, point 2.

TABLE 2

Degree of substitution of various alternan-succinic acid esters, determined by alkaline saponification and acid-base titration.

| Sample name | AlS001 | AlS002 | AlS003 |
|---|---|---|---|
| DS value | 0.034 | 0.089 | 0.161 | c) Turbidity Measurement of Solutions

For the turbidity measurement, the resulting alternan-acetic acid esters were dissolved in different concentrations (see table 3) in water and measured at 525 nm in a spectral photometer.

TABLE 3

Measurement of the turbidity of alternan which has been used as starting material in the reaction, and alternan-succinic acid esters (AlS001, AlS002, AlS003) in solutions comprising different concentrations of said substances.

| | Absorbance at 525 nm Concentration | | |
|---|---|---|---|
| Substance | 0.1% | 0.5% | 1.0% |
| Alternan | 0.048 | 0.213 | 0.399 |
| AlS001 | 0.038 | 0.150 | 0.270 |
| AlS002 | 0.028 | 0.104 | 0.165 |
| AlS003 | 0.027 | 0.070 | 0.089 |

Consideration of the results obtained in example 2b) reveals that the turbidity of solutions comprising alternan-succinic acid esters decreases compared to alternan. The higher the degree of substitution, the lower the turbidity of the solution at the same concentration of the dissolved substances.

d) Molecular Characterization

The molar mass distribution of the resulting alternan-succinic acid esters was analyzed with the help of GPC-MALLS (Gel Permeation Chromatography—Multi Angle Laser Light Scattering) using the agents described under General Methods, point 3. For this, the various substances (alternan, AlS001, AlS002, AlS003) were dissolved in a concentration of in each case 0.2% in demineralized water firstly at room temperature for 24 hours and then at 120° C. for 20 minutes. For all samples, the same refractive index increment (dn/dc) of 0.146 was used. Using this value, recovery rates of ca. 90% in the GPC were obtained for all derivatives.

Figure 1:
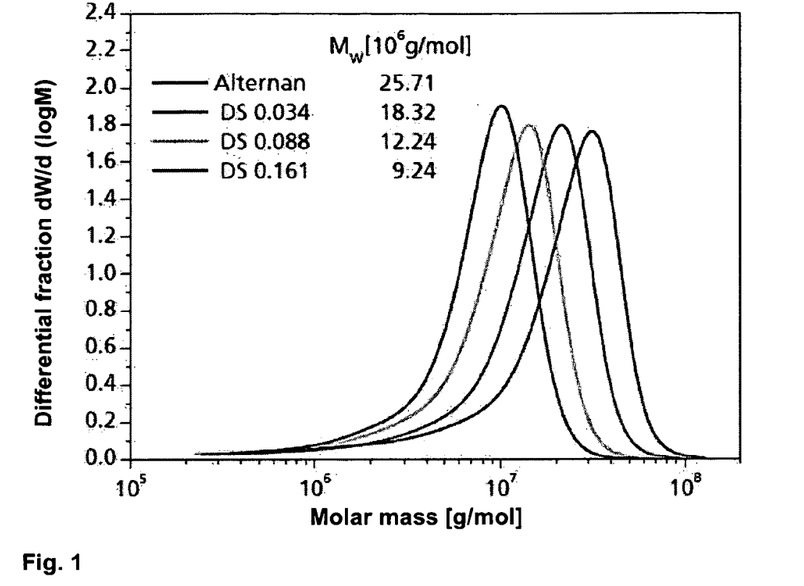
FIG. 1: Molar mass distribution of alternan and alternan-succinic acid esters with different degrees of substitution (DS 0.034, DS 0.088, DS 0.161).

For the weight-average molar mass ($M_w$), the following results were obtained (see also FIG. 1):

TABLE 2

Weight-average molar mass ($M_w$) of alternan-succinic acid esters with different degrees of substitution (AlS001, AlS002, AlS003) and of alternan which has been used as starting material in the reaction (alternan).

| Sample name | Reference | AlS001 | AlS002 | AlS003 |
|---|---|---|---|---|
| $M_w$ [$10^6$ g/mol] | 25.71 | 18.32 | 12.24 | 9.24 | f) Rheological Properties

To determine the rheological properties, the various substances (alternan, AlS001, AlS002, AlS003) were dissolved in a concentration of in each case 5% in demineralized water with stirring at 95° C. The concentration of 5% in each case was chosen because alternan-succinic acid esters of the samples AlS001 and AlS002 were no longer flowable at a concentration of 5%. They formed stable gels in water.

Viscosity

The analysis was carried out with the help of the agents described under General Methods, point 4. The flow behavior (viscosity) of the 5% strength solutions was investigated at 25° C. as a function of the shear rate in the frequency range from $10^0$-$10^2$ Hz.

Figure 2:
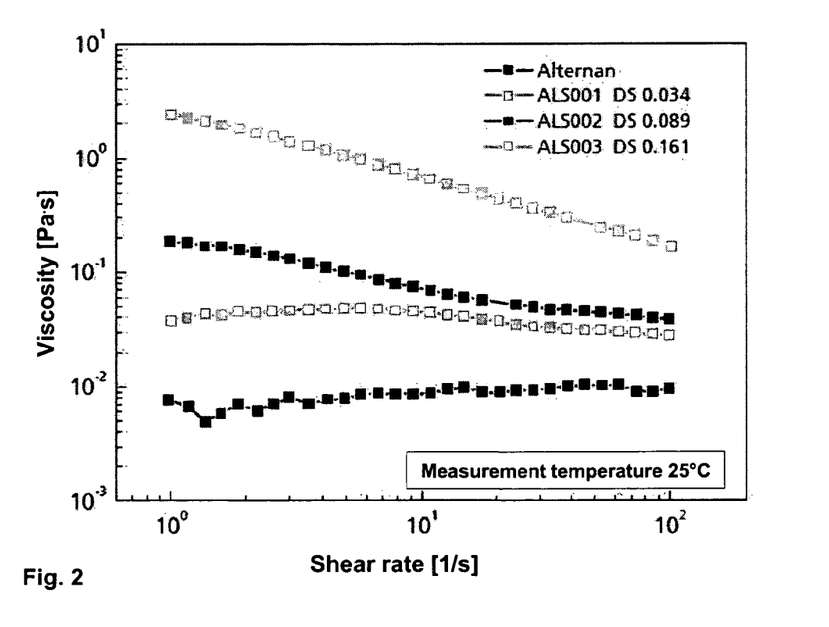
FIG. 2: Comparison of the flow behavior of alternan and alternan-succinic acid esters with different degrees of substitution (DS 0.034, DS 0.088, DS 0.161) at 25° C. The viscosity [Pa×s] is shown as a function of the shear rate [Hz].

FIG. 2 shows a comparison of the flow curves of alternan which has been used as starting material in the esterification reaction and of the flow curves of alternan-succinic acid esters with varying degrees of substitution (AlS001, AlS002, AlS003). With increasing degrees of substitution (DS value), the alternan-succinic acid esters have an increase in the viscosity of the solutions in question. A DS value of 0.161 (AlS003) produced an increase in the viscosity of about 2 orders of magnitude compared to the starting material alternan. Besides the viscosity, the solution state also changed.

The table below gives, by way of example, viscosities of alternan-succinic acid esters which have been measured at different shear rates.

TABLE 3

Viscosities of alternan which has been used as starting material for the carboxylation reaction and alternan-succinic acid esters with different DS values.

| | Shear rate | Alternan | AlS001 | AlS002 | AlS003 |
|---|---|---|---|---|---|
| DS value | | — | 0.034 | 0.089 | 0.161 |
| Viscosity [mPas] | 5 s$^{-1}$ | 7.8 | 48.0 | 102.1 | 1063.1 |
| Viscosity [mPas] | 50 s$^{-1}$ | 10.2 | 30.9 | 44.2 | 247.2 |

Oscillation Measurement by Means of Frequency Sweep

Comparative oscillation measurements of alternan, which was used as starting material in the esterification reaction with the alternan-succinic acid esters with varying degrees of substitution (AlS001, AlS002, AlS003), were established at 25° C. in a frequency range from $10^{-2}$ Hz to $10^1$ Hz using the agents described under General Methods, point 4.

Figure 3:
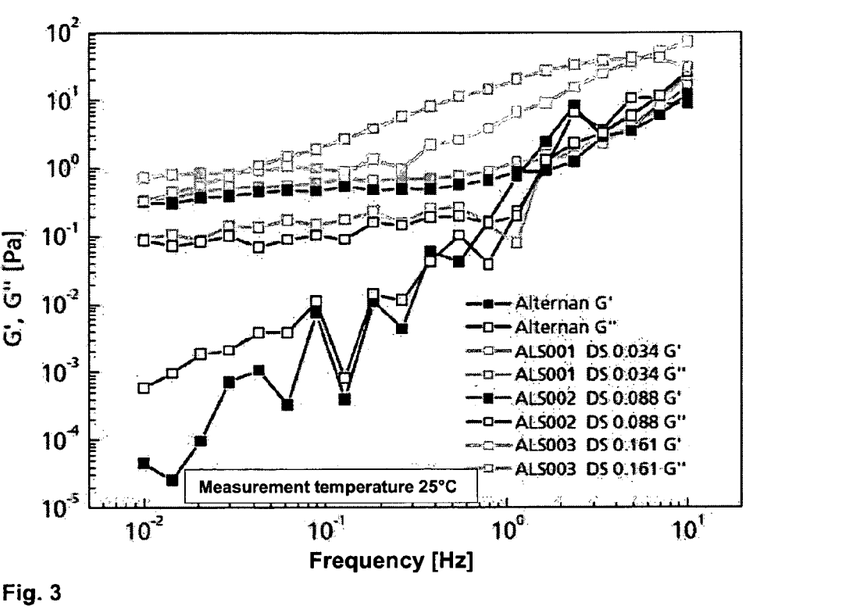
FIG. 3: Frequency sweep of alternan and alternan-succinic acid esters with different degrees of substitution (DS 0.034, DS 0.088, DS 0.161). The storage modulus (G') and the loss modulus (G"), measured in Pascals [Pa] are shown as a function of the frequency [Hz] at constant shear stress.

FIG. 3 shows the results of the comparative frequency sweep between alternan and alternan-succinic acid esters (AlS001, AlS002, AlS003). This shows that alternan has the typical solution character of Newtonian liquids with slight interactions of the dissolved substance. By contrast, alternan-succinic acid esters were gel-like at the same concentration, which is evident from the fact that the elasticity modulus (G') and the loss modulus (G") have a low frequency dependency and that G' is larger than G" (G'>G").

g) Emulsion Behavior

Solutions of different concentration (see table 6) of alternan and alternan-succinic acid esters (AIS001, AIS002) were prepared by homogenizing the substances in question in ultrapure water using an Ultra-Turrax (25 k rpm) for one minute. To in each case 20 ml of these solutions were added in each case 20 ml of sunflower oil. Homogenization for one minute using an Ultra-Turrax (Ultra-Turrax T 25 digital, IKA-Werke GMBH & CO. KG, D-79219 Staufen, Germany) was then carried out at ca. 25 k rpm.

The resulting emulsions were then observed as to whether phase separation occurs.

TABLE 4

Effect of alternan-succinic acid esters (AIS001, AIS002) and alternan on emulsions.

| Substance | Concentration of the substance in the water/oil mixture | Onset of visible phase separation |
|---|---|---|
| Alternan | 0.5% | Directly after homogenization |
| | 2.5% | Directly after homogenization |
| | 5% | Directly after homogenization |
| AIS001 | 0.5% | After ca. 4 hours |
| | 2.5% | After ca. 4 hours |
| AIS002 | 0.5% | After ca. 4 hours |
| | 2.5% | After ca. 4 hours |

Compared to alternan, alternan-succinic acid esters have a stabilizing effect on emulsions.

This shows that alternan-succinic acid esters have a stabilizing effect on emulsions compared to native alternan.

h) Compatibility with Other Gel Formers

Corn Starch

Corn starch was dissolved in demineralized water in a concentration of 5% by boiling under pressure at 150° C. for 20 minutes. By dissolving, with stirring, alternan and various alternan-succinic acid esters (AIS001, AIS003), various mixtures (compositions) containing alternan and alternan-succinic acid esters were prepared from this starch solution. The concentration of alternan or alternan-succinic acid ester in the mixtures was in each case 1%.

Figure 4:
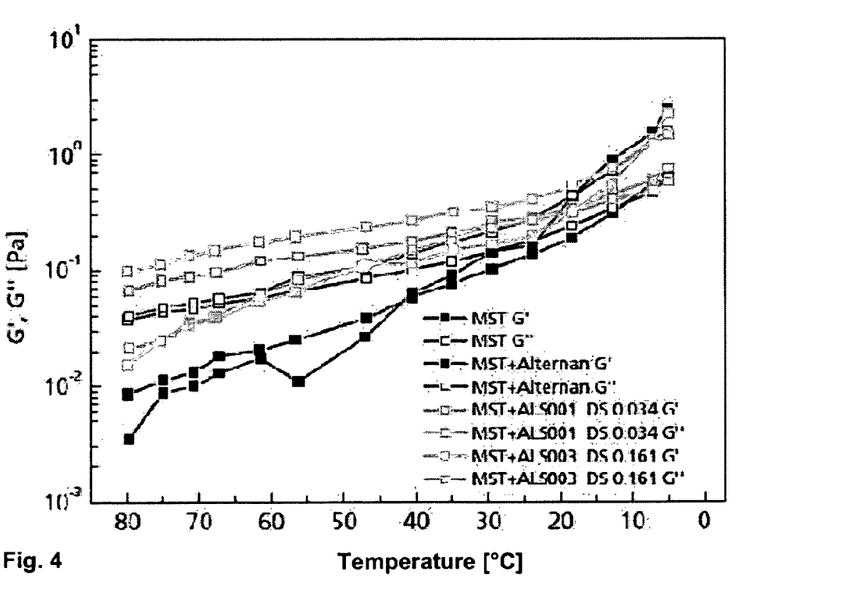
FIG. 4: Gel formation of alternan, alternan-succinic acid esters with different degrees of substitution (DS 0.034, DS 0.088, DS 0.161) and gelatinized corn starch (CST), and mixtures thereof. The storage modulus (G') and the loss modulus (G"), measured in Pascals [Pa], are shown as a function of the temperature [° C.].
Figure 5:
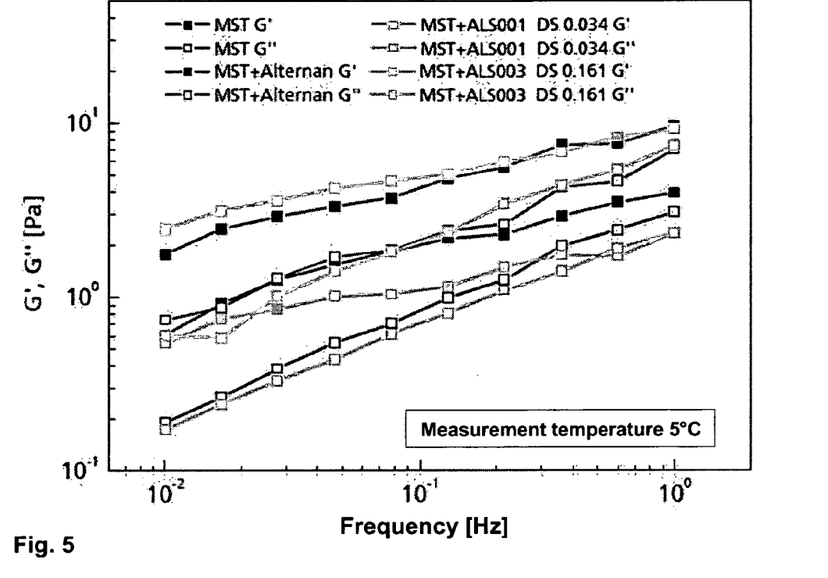
FIG. 5: Comparison of the gel state of alternan, alternan-succinic acid esters with different degrees of substitution (DS 0.034, DS 0.088, DS 0.161) and gelatinized corn starch (CST), and also of mixtures thereof in the frequency sweep. The storage modulus (G') and the loss modulus (G"), measured in Pascals [Pa], are shown as a function of the frequency [Hz] at a measurement temperature of 5° C.
Figure 6:
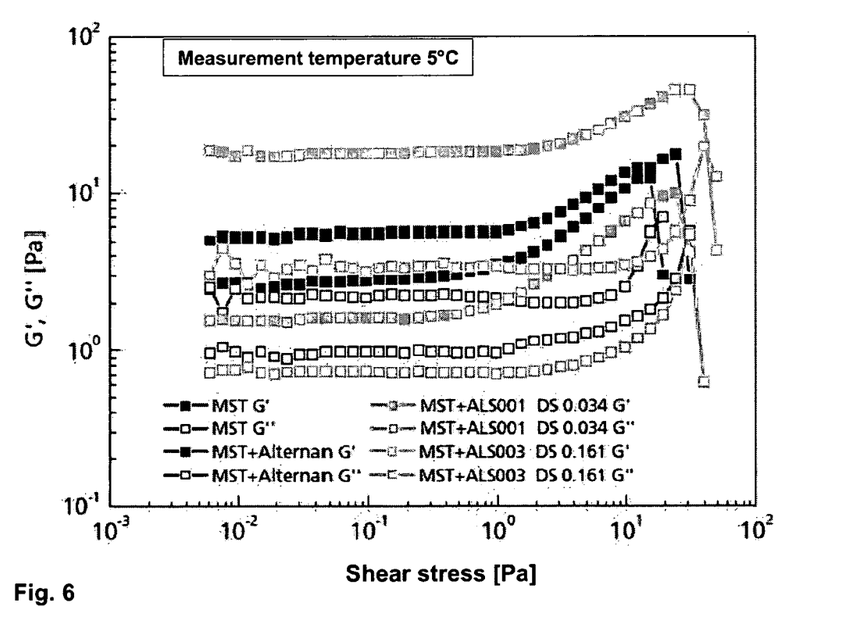
FIG. 6: Comparison of the gel solidity and gel stability of alternan, alternan-succinic acid esters with different degrees of substitution (DS 0.034, DS 0.088, DS 0.161) and gelatinized corn starch (CST), and also of mixtures thereof in the stress sweep. The storage modulus (G') and the loss modulus (G"), measured in Pascals [Pa], are shown as a function of the shear stress [Pa] at a measurement temperature of 5° C.

The hot solution was introduced into the measurement system, heated to 80° C., of the rheometer (see General Methods, point 4). At a frequency of $10^{-2}$ Hz, the gelation of the various mixtures and of a pure starch solution (CST) was monitored during cooling to 5° C. by recording the storage moduli (G') and loss moduli (G") in question (FIG. 4). Following gelation of the mixtures, a frequency sweep (FIG. 5) for estimating the gel state and a stress sweep (FIG. 6) for assessing the gel solidity and the shear stability were recorded at a temperature of in each case 5° C.

The cooling curves (FIG. 4) reveal for all solutions that, at 80° C., the storage modulus (G') is lower than the loss modulus (G"). As cooling increases, the respective values for G' and G" increase. At about 10° C., G' and G" for all solutions achieve identical or at least approximately identical values, i.e. in this temperature range, the sol-gel transition takes place in the respective samples (gelation point). Solutions comprising mixtures of corn starch and alternan or alternan-succinic acid ester have approximately the same gelation point. The addition of alternan-succinic acid esters to corn starch solutions increases both elastic, and also viscous, fractions of the starch solution, which in the present experiment is most pronounced in the case of the mixture (composition) of corn starch (CST) and the alternan-succinic acid ester with the name AIS003.

From the frequency sweep (FIG. 5) it can deduced that all of the mixtures formed stable gels at a temperature of 5° C.

From the stress sweep (FIG. 6) it can be deduced that the addition of alternan reduces the gel solidity of corn starch gels, whereas the addition of alternan-succinic acid esters, particularly those with relatively high degrees of substitution (e.g. the substance AIS003), increases the gel solidity of corn starch gels.

Stability in Foods

Solutions of varying concentration (see table 5) of alternan-succinic acid esters (AIS001, AIS002, AIS003) were prepared by homogenizing the substances in question in standard commercial milk using an Ultra-Turrax (Ultra-Turrax T 25 digital, IKA-Werke GMBH & CO. KG, D-79219 Staufen, Germany) at a speed of ca. 25 k rpm for one minute. The resulting solutions were then observed over several hours up to one day as to whether all of the constituents remained in solution, or whether inhomogeneous areas formed and/or whether precipitates arose.

TABLE 5

Stability of solutions of the alternan-succinic acid esters in milk

| Substance | Concentration of the substance in the solution | Observation |
|---|---|---|
| AIS001 | 1% | Stable, homogeneous mixture |
| | 5% | Stable, homogeneous mixture |
| AIS002 | 1% | Stable, homogeneous mixture |
| | 5% | Stable, homogeneous mixture |
| AIS003 | 1% | Stable, homogeneous mixture |
| | 5% | Stable, homogeneous mixture |

3. Alternan-Octenylsuccinic Acid Ester (Alternan-Octenylsuccinate)

a) Preparation

Firstly, 60 ml of demineralized water were introduced into a 250 ml beaker and then 10 g of alternan were dissolved with continuous stirring using a magnetic stirrer. After dissolving the alternan, the pH was adjusted to 8.5 by adding 0.5M NaOH solution (Merck).

In mixtures separate from one another, either 1 ml or 2 ml of octenylsuccinic anhydride (OSA) was then continuously metered in by means of a burette over the course of one hour. The various reaction mixtures were then stirred either for one further hour or for three further hours, resulting in a total reaction time for the individual mixtures of 2 or 4 hours (also see table 8 in this regard). Throughout the entire reaction time, the pH was kept constant by using a 0.5M NaOH solution (Merck) using an automated titrater (pH-Stat, Metrohm 719 S Titrino). The reactions were carried out at 23° C.

The reaction was ended by neutralization (pH 6.3) with the help of 0.5M HCl (Merck), and, to precipitate out the alternan, the reaction mixture was poured into a 500 ml beaker with twice the volume of ethanol (denatured, Monopoly Administration). After stirring for 5 minutes using a magnetic stirrer, the alternan derivative was separated off from the mixture with the help of a vacuum suction filter ($\phi$ 100 mm), then the filter cake was resuspended for washing in ca. 100 ml of ethanol/demineralized water (80:20; v:v). The washing procedure was repeated twice, then the filter cake was granulated using a laboratory sieve ($\phi$ 200 mm, mesh width 3 mm) and then the granules were dried in the air for two days. Prior to the characterization of the product, the agglomerates were comminuted using a laboratory mill (IKA model A 10).

b) Characterization

Turbidity Measurement

The turbidity measurement was carried out with in each case a 0.5% strength solution comprising alternan or the various alternan-octenylsuccinic acid esters. For their preparation, 49.75 g of demineralized water were weighed in each case into a 150 ml beaker, and 0.25 g of the corresponding substance was stirred therein at room temperature and with continuos stirring using a magnetic stirrer. The turbidity was measured after stirring for 1 hour with the help of a photometer (PM 200 from Rühle, Berlin) using a 525 nm filter and a cell with a thickness of 1 cm. The absorbance value has been given in each case.

Emulsifying Capacity

The emulsifying capacity of alternan and of the alternan-octenylsuccinic acid esters prepared under various conditions was determined by in each case initially introducing 20 ml of a 1% strength solution (stock solution: 0.5 g+49.5 g of demineralized water) into a 100 ml titration beaker (from Mettler titrators), then adding 20 ml of sunflower oil (standard commercial oil from REWE) and initially homogenizing the mixture using an Ultra-Turrax (T 18) at 14 000 rpm for 1 minute. Then, in each case 10 ml of oil were added stepwise, which had in each case been homogenized for 1 minute (Ultra-Turrax, 14 000 rpm). The addition of oil was carried out until the viscosity of the emulsion decreased and/or the emulsion broke.

The emulsifying capacity was calculated according to the following formula:

Emulsifying capacity [ml of oil/g of alternan×100 ml of water]=total volume of oil×5

The results shown in the table below were obtained.

TABLE 6

Turbidity measurement (column 4) and amount emulsifying capacity (column 5) of alternan and alternan-octenylsuccinic acid esters which have been prepared by various processes.

| Sample | Amount of octenylsuccinic anhydride | Reaction time | Turbidity | Emulsifying capacity |
|---|---|---|---|---|
| Reference | — | — | 0.302 | 125 ml oil/g |
| Sample 2 | 1 ml | 2 h | 0.167 | 300 ml oil/g |
| Sample 1 | 1 ml | 4 h | 0.105 | 300 ml oil/g |
| Sample 3 | 2 ml | 2 h | 0.105 | 350 ml oil/g |
| Sample 4 | 2 ml | 4 h | 0.109 | 350 ml oil/g |

The amount of octenylsuccinic anhydride used in the esterification reaction and the reaction time are shown in columns 2 and 3, respectively (for further reaction parameters see example 3a)). The reference (column 1) referred to is native alternan which was used as starting material in the reaction. Samples 1, 2, 3 and 4 (column 1) refers to alternan-octenylsuccinic acid esters which have been prepared by means of stated different reaction conditions.

The emulsifying capacity of alternan-octenylsuccinic acid esters is increased compared to alternan. The turbidity of solutions comprising alternan-octenylsuccinic acid ester is reduced compared to alternan at identical concentration.

4. Emulsifying Properties of Alternan-Octenylsuccinic Anhydride a) Preparation of Alternan-Octenylsuccinic Anhydride Alternan was reacted with octenylsuccinic anhydride in the ratio 1:0.05 in the alkaline medium and neutralized when the reaction was complete. The resulting alternan-octenylsuccinic acid ester was precipitated out with ethanol, washed and dried.

The degree of substitution (DS) of the alternan-octenylsuccinic acid ester ascertained by means of the method described under General Methods, point 2 was 0.024. These alternan-octenylsuccinic acid esters have been analyzed below.

b) Molecular Characterization

Figure 8:
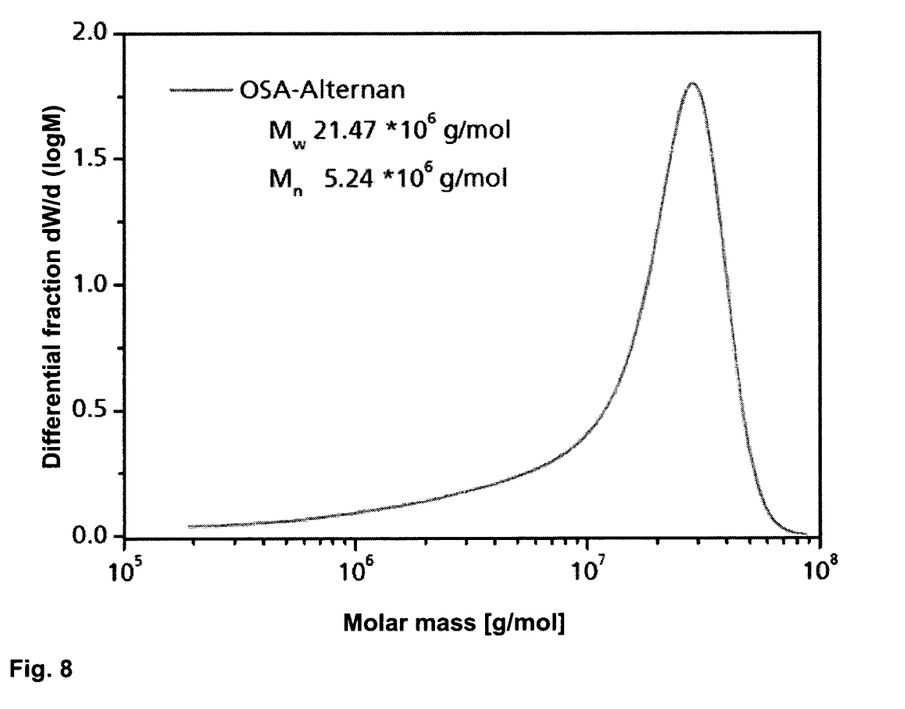
FIG. 8: Molar mass distribution of alternan-octenylsuccinic acid esters with a degree of substitution of 0.024.

The molar mass distribution of the resulting alternan-succinic acid esters was analyzed with the help of GPC-MALLS (Gel Permeation Chromatography-Multi Angle Laser Light Scattering) using the agents described under General Methods, point 3 (FIG. 8). The resulting average molar mass ($M_w$) was $21.5 \times 10^6$ g/mol.

c) Rheological Properties

Viscosity Using a Rheometer

The analysis was carried out with the help of the means described under General Methods, point 4. The flow behavior (viscosity) of the 10% strength solutions was investigated at 20° C. as a function of the shear rate in the frequency range shown (FIG. 9).

Alternan-octenylsuccinic acid esters exhibited viscosity of ca. 25 mPa×s, which was slightly higher than the viscosity of alternan (ca. 15 mPa×s).

Viscosity Using an RVA

The viscosities of alternan and alternan-octenylsuccinic acid esters were determined compared to the viscosity of gum arabic with the help of an RVA (Rapid Visco Analyzer) using the method given under point 5, General Methods. In each case, 10% strength solutions (w/v) were used. The results are shown in the table below.

TABLE 9

Viscosities, ascertained with an RVA, of gum arabic, alternan and alternan-octenylsuccinic acid ester.

| | Viscosity [mPa × s] | | |
|---|---|---|---|
| Substance | after 30 s | after 60 s | 60 s to 300 s |
| Gum arabic | 120 | 0 | 0 |
| Alternan | 40 | 120 | 120 |
| Alternan-octenylsuccinic acid ester | 250 | 250 | 250 | d) Emulsifying Properties of Alternan-Octenylsuccinic Anhydride

Figure 7:
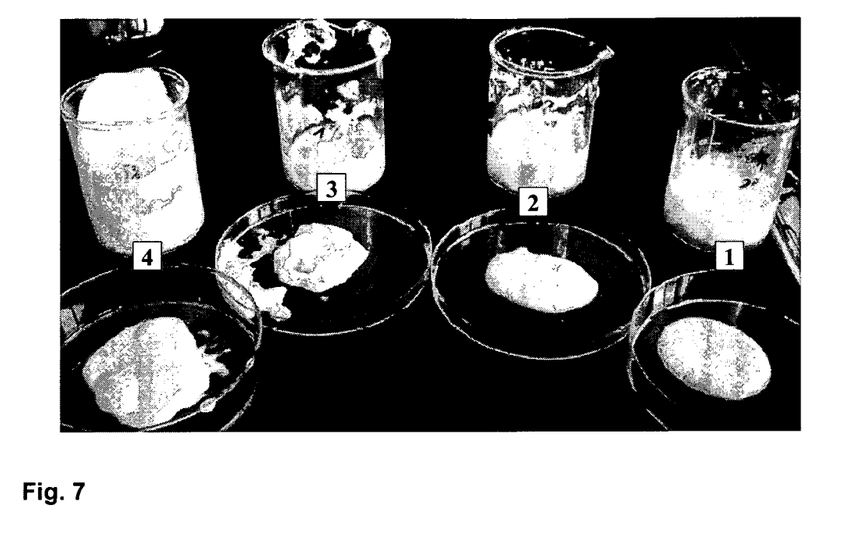
FIG. 7: Photograph of the emulsions which were obtained with different concentrations of alternan-octenylsuccinic acid esters (see also table 10).

In each case 20 mg, 40 mg, 200 mg and 1 g of alternan-octenylsuccinic acid ester (Al-OSA) were dissolved in 20 ml of demineralized water with the help of an Ultra-Turrax (1 minute, (Ultra-Turrax T 25 digital, IKA-Werke GMBH & CO. KG, D-79219 Staufen, Germany) at ca. 25 k rpm). 20 ml of sunflower oil (commercial product: ja! from REWE) were then added. The resulting mixture was homogenized by treatment for one minute using an Ultra-Turrax (see above). The consistency and the stability of the consistency were then assessed. FIG. 7 shows a diagram of the resulting emulsions. Further results are summarized in the table below.

TABLE 10

Consistency and stability of oil/water mixtures comprising different amounts of alternan-octenylsuccinic acid ester (Al-OSA).

| Amount of substance in the mixture | | | | Phase separa- | |
|---|---|---|---|---|---|
| Water [ml] | Oil [ml] | Al-OSA [mg] | Consistency/deposition of oil droplets | tion after ca. 72 h | No. in FIG. 7 |
| 20 | 20 | 20 | Emulsion beaten egg whites-like/increased | none | 1 |
| 20 | 20 | 40 | Emulsion, beaten egg whites-like/slight | none | 2 |

TABLE 10-continued

Consistency and stability of oil/water mixtures comprising different amounts of alternan-octenylsuccinic acid ester (Al-OSA).

| Amount of substance in the mixture | | | | Phase separa- | |
|---|---|---|---|---|---|
| Water [ml] | Oil [ml] | Al-OSA [mg] | Consistency/deposition of oil droplets | tion after ca. 72 h | No. in FIG. 7 |
| 20 | 20 | 200 | Emulsion, beaten egg whites-like/none | none | 3 |
| 20 | 20 | 1000 | Emulsion, creamy/none | none | 4 |

Column 6 contains the name (No.) of the corresponding mixtures, as stated in FIG. 7.

e) Comparison of the Emulsifiability of Alternan-Octenyl-succinic Acid with Gum Arabic In each case 3% strength aqueous solutions (w/v) of alternan-octenylsuccinic acid or gum arabic were prepared. To these solutions were added different amounts of standard commercial sunflower oil before a homogenization was carried out using an Ultra-Turrax (Ultra-Turrax T 25 digital, IKA-Werke GMBH & CO. KG, D-79219 Staufen, Germany, 1 minute at 9 k rpm). After a period of six days, the resulting emulsions were assessed as to the stability of the emulsion. The results obtained are shown in the table below.

TABLE 11

Stability of emulsions with gum arabic and alternan-octenylsuccinic acid ester.

| Amount of substance in the mixture | | | Phase separation after 5 days | |
|---|---|---|---|---|
| Water [ml] | Oil [ml] | Emulsifier [mg] | Gum arabic | Alternan-octenylsuccinic acid ester |
| 18 | 2 | 600 | significant separation | none |
| 15 | 5 | 600 | significant separation | none | f) Emulsions with Varying Concentrations of Alternan-Octenylsuccinic Acid Ester

Aqueous solutions with different concentrations of alternan-octenylsuccinic acid ester were prepared. To these solutions were then added different amounts of standard commercial sunflower oil before a homogenization was carried out using an Ultra-Turrax (Ultra-Turrax T 25 digital, IKA-Werke GMBH & CO. KG, D-79219 Staufen, Germany, 1 minute at 9 k rpm). After a period of six days, the resulting emulsions were assessed as to the stability of the emulsion. The results obtained are shown in the table below.

TABLE 12

Stability of emulsions with varying oil content with different amounts of alternan-octenylsuccinic acid (Al-OSA) after 6 and 18 days.

| Amount of substance in the mixture | | Phase separation at the amounts of Al-OSA in the mixture stated in each case | | | | | |
|---|---|---|---|---|---|---|---|
| Water [ml] | Oil [ml] | 5 mg | 10 mg | 30 mg | 50 mg | 100 mg | 500 mg | |
| 10.0 | 0.1 | none | none | none | none | none | none | after |
| 9.7 | 0.3 | none | none | none | none | none | none | 18 days |
| 9.5 | 0.5 | complete | significant | none | none | none | none | |
| 9.0 | 1.0 | complete | complete | none | none | none | none | |
| 8.0 | 2.0 | — | complete | — | none | none | — | after |
| 7.0 | 3.0 | — | complete | — | significant | none | — | 6 days | g) Preparation of Creams

Alternan-octenylsuccinic acid esters were added to a mixture of water comprising 30% (v/v) standard commercial sunflower oil up to an end concentration of 15% (w/v) and homogenized using an Ultra-Turrax (9 k rpm) for 1 minute. A stable cream was obtained. Similar results were obtained with a water/oil mixture comprising 36% sunflower oil. In contrast to the cream prepared from the mixture comprising 30% oil, that prepared from the mixture with 36% oil was more creamy.

The invention claimed is:

1. An alternan-carboxylic acid ester.

2. A method of preparing an alternan-carboxylic acid ester comprising reacting alternan with a carboxylic acid or its anhydride, a carboxylic acid halide, or a vinyl ester.

3. An emulsifier comprising the alternan-carboxylic acid ester of claim 1.

4. An emulsion comprising the emulsifier of claim 3.

5. A composition comprising the alternan-carboxylic acid ester of claim 1.

6. A cleaning composition comprising the alternan-carboxylic acid ester of claim 1.

7. A method of preparing food, cosmetic, or pharmaceutical composition comprising admixing the composition of claim 5 with at least one food item, cosmetic item, or pharmaceutically active substance.

8. A composition comprising the emulsifier of claim 3.

9. A composition comprising the emulsion of claim 4.

10. The method of claim 7, wherein the alternan-carboxylic acid ester acts as a surfactant.

11. The method of claim 10, wherein the surfactant is a foaming agent.

12. The method of claim 10, wherein the surfactant is a body care substance.

13. An alternan-carboxylic acid ester, wherein said alternan-carboxylic acid ester has emulsifying properties.

14. A modified alternan which is an alternan-carboxylic acid ester.

15. An alternan-carboxylic acid ester depicted by the following formula where R is a straight-chain or branched alkyl residue having 1 to 11 carbon atoms, which can carry one or more oxo, hydroxy, carboxy residues or a straight-chain or branched alkenyl residue having 1 to 11 carbon atoms, which can carry one or more oxo, hydroxy, carboxy residues.

16. An emulsifier comprising the alternan-carboxylic acid ester of claim 15.

17. An emulsion comprising the emulsifier of claim 16.

18. A composition comprising the alternan-carboxylic acid ester of claim 15.

19. A composition comprising the emulsifier of claim 16.

20. A composition comprising the emulsion of claim 17.

21. An alternan-carboxylic acid ester, depicted by the following formula where R is a straight-chain or branched alkyl residue having 1 to 11 carbon atoms, which can carry one or more oxo, hydroxy, carboxy residues or a straight-chain or branched alkenyl residue having 1 to 11 carbon atoms, which can carry one or more oxo, hydroxy, carboxy residues, wherein said alternan-carboxylic acid ester has emulsifying properties.

22. The alternan-carboxylic acid ester of claim 1, which is an alternan-acetic acid ester, alternan-succinic acid ester, or an alternan-octenylsuccinic acid ester.

23. An emulsifier comprising the alternan-carboxylic acid ester of claim 22.

24. An emulsion comprising the emulsifier of claim 23.

25. A composition comprising the alternan-carboxylic acid ester of claim 22.

26. A composition comprising the emulsifier of claim 23.

27. A composition comprising the emulsion of claim 24.

28. The alternan-carboxylic acid ester of claim 22, wherein said alternan-carboxylic acid ester has emulsifying properties.

29. A method of preparing an alternan-carboxylic acid ester comprising reacting alternan with straight-chain or branched alkyl carboxylic acid or its anhydride, or a straight-chain or branched alkenyl carboxylic acid or its anhydride, or a straight-chain or branched alkyl or alkenyl carboxylic acid halide, or a straight-chain or branched alkyl or alkenyl vinyl ester.

30. A method of preparing an alternan-carboxylic acid ester comprising reacting alternan with acetic acid or its anhydride or halide, or with succinic acid or its anhydride or halide, or with octenylsuccinic acid or its anhydride or halide or with vinyl acetate or with vinyl succinate or with vinyl octenylsuccinate.

31. A cleaning composition comprising the alternan-carboxylic acid ester of claim 15.

32. A cleaning composition comprising the alternan-carboxylic acid ester of claim 22.

33. A method of preparing food, cosmetic, or pharmaceutical composition comprising admixing the composition of claim 18 with at least one food item, cosmetic item, or pharmaceutically active substance.

34. A method of preparing food, cosmetic, or pharmaceutical composition comprising admixing the composition of claim 25 with at least one food item, cosmetic item, or pharmaceutically active substance.

35. The method of claim 33, wherein the alternan-carboxylic acid ester acts as a surfactant.

36. The method of claim 34, wherein the alternan-carboxylic acid ester acts as a surfactant.

37. The method of claim 35, wherein the surfactant is a foaming agent.

38. The method of claim 36, wherein the surfactant is a foaming agent.

39. The method of claim 35, wherein the surfactant is a body care substance.

40. The method of claim 36, wherein the surfactant is a body care substance.

* * * * *